(12) United States Patent  
Edens et al.

(10) Patent No.: US 6,368,595 B2  
(45) Date of Patent: Apr. 9, 2002

(54) TOPICAL APPLICATION OF ENZYMES USING A PEELABLE FILM

(75) Inventors: Luppo Edens, Rotterdam; Bertus Noordam, s-Gravenzande, both of (NL)

(73) Assignee: Cosmoferm B.V., Ma Delft (NL)

( * ) Notice: Subject to any disclaimer, the term of this patent is extended or adjusted under 35 U.S.C. 154(b) by 0 days.

(21) Appl. No.: 09/380,805

(22) PCT Filed: Jan. 8, 1999

(86) PCT No.: PCT/EP99/00245

§ 371 Date: Oct. 25, 1999

§ 102(e) Date: Oct. 25, 1999

(87) PCT Pub. No.: WO99/34774

PCT Pub. Date: Jul. 15, 1999

(30) Foreign Application Priority Data

Dec. 22, 1998 (EP) ............................................... 98204469

(51) Int. Cl.$^7$ ................................................ A61K 38/46

(52) U.S. Cl. ..................... 424/94.6; 424/401; 424/94.1; 424/443; 424/444; 424/78.03

(58) Field of Search ............................... 424/401, 78.03, 424/443, 444, 94.1, 94.6

(56) References Cited

U.S. PATENT DOCUMENTS

| 4,098,435 A | 7/1978 | Weyn ........................... 222/94 |
| 4,487,757 A | 12/1984 | Kiozpeoplou ............... 424/7.1 |

FOREIGN PATENT DOCUMENTS

| DE | 3 630 849 | 3/1987 |
| DE | 93 07 726.2 | 9/1993 |
| FR | 2.051.922 | 4/1971 |
| JP | 57-73098 | 7/1982 |
| JP | 61-268611 | 11/1986 |
| JP | 61268611 | * 11/1986 |
| WO | WO 95/28092 | 10/1995 |

* cited by examiner

Primary Examiner—Jose' G. Dees  
Assistant Examiner—Konata M. George  
(74) Attorney, Agent, or Firm—Morrison & Foerster LLP

(57) ABSTRACT

The present invention discloses a method for topical application of an enzyme, wherein the enzyme becomes incorporated in a peelable film, for instance a polyvinyl alcohol film, after its application. In this way, the release of enzyme-containing dust particles from the site of application is prevented.

7 Claims, 2 Drawing Sheets

— Powder

— Liquid

TOPICAL APPLICATION OF ENZYMES USING A PEELABLE FILM

FIELD OF THE INVENTION

The present invention relates to the field of topical application of an enzyme-containing composition.

BACKGROUND OF THE INVENTION

Enzymes are used in a number of consumer products, among which are detergents and cosmetics. A problem associated with enzyme-containing products is that enzymes may induce allergic sensitization upon inhalation of airborne dust or aerosols. For instance, after topical application of an enzyme-containing cream, enzyme-containing dust particles may be released from the site of application when the cream is dried.

One solution to prevent inhalation of enzyme-containing dust particles is to immobilize the enzyme before its actual application (see Japanese patent applications J57073098 and J61268611). However, the activity of an immobilized enzyme towards a solid substrate (the skin) is known to be quite low. For instance, immobilized proteases are not expected to interact with stratum corneum proteins.

It would therefore be desirable to apply a composition containing an enzyme in a non-immobilized form in such a way that release of dust particles from the site of application would not occur.

The present invention provides a convenient solution to the above problems by providing a method for topical application of an enzyme, wherein the release of enzyme-containing dust-particles from the site of application is prevented whereas enzyme activity is guaranteed.

DESCRIPTION OF THE INVENTION

The present invention discloses a method for topical application of an enzyme-containing composition, wherein an enzyme composition is applied which additionally comprises a film-forming agent. Upon topical application of said composition, the film-forming agent allows for the formation of a peelable film incorporating the enzyme, due to evaporation of the solvent(s) used. After evaporation of the solvent and after the enzyme has fulfilled its task, the film incorporating the enzyme is removed from the site of application. In this way, the release of enzyme-containing dust particles, which easily are formed upon drying of an enzyme-containing composition at the site of application, is prevented.

Specifically, the method of the invention comprises the steps of:
  preparing a composition which comprises an enzyme and a film-forming agent,
  topically applying said composition,
  incubating said composition on the site of application for a sufficient time period to enable formation of a film incorporating the enzyme, and
  removing said film incorporating the enzyme from the site of application.

In one embodiment of the invention, the composition comprising an enzyme and a film-forming agent is prepared by mixing two separate compositions, i.e. a first composition comprising the enzyme and a second composition comprising the film-forming agent. In this way, the enzyme is not detrimentally influenced by the presence of the dissolved film-forming agent or by the presence of any auxiliary agent.

A preferred option of this embodiment comprises the packaging of the said two individual compositions in a dual component dispensing system. Using a dual component dispensing system, simultaneous delivery of a composition comprising the enzyme and a composition comprising the film-forming agent is possible. Upon delivery, both individual compositions are mixed, either in situ or in the dispensing system. Mixing of both compositions results in a final composition comprising the enzyme and the film-forming agent in a form which is suitable for direct use.

The dispensing system to be used in this embodiment of the invention is not critical. Any system can be used which allows for the separate containment of the enzyme composition and the composition comprising the film-forming agent.

For instance, a dispensing system can be selected from the dual component dispensing systems which have been developed for the packaging and delivery of non-compatible chemical compounds, i.e. chemical compounds which react with each other when brought into contact. For instance, dual component dispensers are known from the field of adhesives.

Apart from adhesives, multicomponent dispensing systems have also been described for the formulation of incompatible compounds in toothpaste. Flexible two-compartment dentrifice tubes are described in U.S. patents U.S. Pat. No. 4,487,757 and U.S. Pat. No. 4,098,435. A two-compartment tube for the storage of a non-aqueous enzyme composition separate from the aqueous toothpaste composition has been described in FR 2,051,922.

In yet another but basically very simple approach, one pair of plastic pouches provides material for single use only. The outlets of the two pouches are close to each other and discharge of the contents can be effectuated by tearing open the end pieces of the pouch (German patent application DE 3 630 849).

Furthermore, German "Gebrauchsmuster" DE, U, 93 07 726 mentions a two-chamber packaging unit in which the two separately packed components can be mixed by applying pressure on one of the chambers. Only after mixing is complete, the package is opened to release the freshly prepared mixture.

The commercially available container shown in FIG. 1 is also suitable. In this container, the enzyme composition, e.g. in the form of a lyophilized powder, is present in an insert placed on top of a vial. Pushing the cap downwards pierces the membrane separating the enzyme composition and the composition comprising the film-forming agent. Upon shaking, the enzyme composition and the film-forming composition are mixed and subsequently are applied.

Using the containers shown in FIGS. 2A and B, the same complete mixing approach is obtained. The container of FIG. 2A is a conventional tube comprising the composition with the film-forming agent, additionally containing a small sachet or ampulla containing the enzyme in a stabilized form. The container of FIG. 2B is a two-compartment sachet, wherein both compartments are separated by a breakable membrane. Just before use, the sachet or ampulla is opened or broken by bending or pressing in such a way that the stabilized enzyme is released. After thorough mixing of the enzyme with the composition comprising the film-forming agent, the tube or sachet is opened and its contents topically applied.

The enzyme to be used in the method of the invention will depend on the desired application. Suitable enzymes typically are found in the classes of oxidoreductases, transferases, hydrolases and/or isomerases. For example, the enzyme is a glucose oxidase, peroxidase, lipoxygenase, superoxide dismutase, tyrosinase, protease, phosphatase, phytase, glycosidase, glucanase, lysozyme, esterase, lipase, phospholipase, sulfatase, urease, transglutaminase or protein disulfide isomerase. It is also possible to apply a composition comprising a mixture of two or more enzymes.

A preferred enzyme for use in the method of the invention is a protease.

The way in which the enzyme is formulated is not critical for the invention. The enzyme may be formulated as a solid or as a liquid composition. A liquid composition may for instance be an aqueous composition wherein the enzyme is solubilized and, preferably, stabilized, or may be a suspension wherein a solid form of the enzyme is suspended in a liquid. Alternatively, the enzyme may be formulated as an oil-in-water emulsion or as a water-in-oil emulsion. In both emulsion types, the enzyme is present in the aqueous phase, preferably in a stabilized form. Furthermore, the enzyme can be presented as an essentially dry powder, optionally suspended in a non-aqueous liquid. The nature of the enzyme composition may thereby depend on, for instance, the desired application.

In a preferred embodiment of the invention, the enzyme composition is an aqueous composition wherein the enzyme is solubilized. To stably formulate an enzyme in an aqueous composition, the enzyme composition preferably comprises a sufficient amount of a water activity lowering agent. For instance, a polyol may be used for stabilization.

In that regard, the choice of the polyol which is used to stabilize an aqueous enzyme composition is not critical for the invention. Any polyol which is known to the skilled person to effectively stabilize an enzyme in an aqueous solution can be used. Polyols that are particularly useful are polyols selected from the group of glycerol, sorbitol, propylene glycol, maltodextrins, or a sugar such as sucrose, lactose, glucose or trehalose. For topical applications, one should consider a polyol which is acceptable for topical use, i.e. glycerol, polyethylene glycol, butylene glycol, propylene glycol, trehalose or sorbitol.

The polyol is used in a high concentration, i.e. a concentration which results in a sufficiently low water activity in the enzyme composition to adequately stabilize the enzyme. It is known in the art that these concentrations may somewhat vary with the polyol used. Preferably, the polyol is used in a concentration of 20–100%, more preferably in a concentration of 30–90%, even more preferably in a concentration of 40–90%, even more preferably in a concentration of 50–90%, most preferably in a concentration of 60–80%.

Such a stable aqueous composition can also be used to produce, when combined with a suitable emulsifier, either a water-in-oil emulsion (see WO 95/28092) or an oil-in-water emulsion.

In another preferred embodiment of the invention, the enzyme composition is an aqueous composition which is a suspension of the enzyme in a precipitated form. For instance, the enzyme is precipitated by the addition of a high concentration of a salt, such as ammonium sulphate.

The film-forming agent can be any agent which allows for both the formation of a peelable mask (peelable film) upon evaporation of solvent occurring after topical application of the composition comprising the enzyme and the film-forming agent as well as the release of 90% or more of the enzyme being incorporated in said peelable film.

For instance, the film-forming agent can be a soluble or dispersible colloid, including a broad range of polymeric compounds like polyvinyl alcohol, acrylic (co)polymers, polyurethane, latex, polyvinylpyrrolidone, hydrocolloids like gum karaya or alginate, and the like. The choice of the film-forming agent to be used may among others be dependent on the enzyme which is intended to be topically applied. Said choice further may be dependent on the desired solubility, tacticity, plasticity, rheology, and drying time. Apart from these aspects, shelf stability may also taken into account.

A preferred film-forming agent to be used in the composition according to the invention is polyvinyl alcohol (PVA). It is generally known to the skilled person that the properties of a PVA film will mainly depend on the type of PVA which is used for its preparation. The properties of the various types of PVA are mainly governed by the molecular weight (degree of polymerization) and the remaining content of acetyl groups (see for instance the Hoechst High Chem brochure on Mowiol PVA, as can be obtained from Clariant Benelux, Amsterdam, the Netherlands).

The specific type of PVA which may be selected is also dependent on the general aspects taken into account for the choice of a specific film-forming agent.

If desired, mixtures of different PVA types may be applied to obtain a film having optimal characteristics.

For instance, a suitable PVA for use in combination with an aqueous enzyme-containing composition is a PVA which gives a satisfactory viscosity in the presence of a substantial amount of water. The viscosity of a PVA formulation thereby typically will depend on the type of PVA as well as the concentration of the PVA.

In addition to a film-forming agent, compounds may be present in the composition according to the invention which may influence the properties of the composition and/or the resulting film.

For instance, to obtain a very viscous solution, a suitable viscosifier, such as xanthan or hydroxyethylcellulose may be added.

A high amount of water in the composition according to the invention allows the enzyme to act on the skin for a relatively long time period. However, a relatively short drying time may be more convenient for the user. To shorten the drying time of the PVA solution, it may be an option to lower the water content of the formulation. For instance, the aqueous phase of the composition may further contain a solvent to hasten evaporation, like ethanol.

To lower the water content of the formulation even further, a low viscous PVA grade, for instance Mowiol 3-83 or 4-88 (Clariant), can be used, since a low viscous PVA grade may be applied in a relatively high concentration. With these low viscous PVA grades solutions up to 35% (w/w) in water yield an acceptable spreadability. A withcoming advantage of such relatively high PVA concentrations is an increased tear strength of the film formed upon drying.

To produce a film with a varying degree of plasticity, a plasticizing agent may be used, like glycerol, sorbitol, ethylene glycol.

To minimize tacticity, a so-called adhesion reducer may be added. Examples of such compounds are silicone oil or certain waxes. To increase tacticity, certain cosmetically acceptable compounds like for example honey may be added.

To improve spreadability, drying behaviour and removability, the composition of the invention may comprise a surfactant functioning as a wetting agent, e.g. a non-ionic surfactant, like Tween 20, and/or a betaine.

The PVA is applied in the formulation in a concentration which may vary from 0.1–40%. A high viscosity PVA grade, like Mowiol 40-88 (Clariant), typically is applied in the lower concentration ranges, e.g. from 0.1–20%, preferably from 1–10%, whereas a low viscosity PVA grade, like Mowiol 3-83 or 4-88, typically is applied in the higher ranges, e.g. from 20–40%, preferably from 25–30%.

The composition according to the invention may include other active ingredients next to an enzyme and a film-forming agent.

For instance, the composition according to the invention may include a substrate for the enzyme which is present in the composition. Examples are linoleic or linolenic acid as a substrate for lipoxygenase; casein as a substrate for transglutaminase; hydrogen peroxide as a substrate for peroxidase; vitamin precursors as a substrate for esterases/lipases.

In addition, the composition according to the invention may include an active ingredient which acts synergistically with the enzyme of interest.

It is up to the choice of the skilled person whether the additional active ingredient is present in composition comprising the film-forming agent or in the enzyme composition. Certain active ingredients, such as a substrate for the enzyme of interest, preferably are present in the composition comprising the film-forming agent.

Specific cosmetic preparations further include the usual components.

The composition comprises a vehicle to enable the active ingredient to be conveyed to the skin. Vehicles include water, solids and liquids. These are classified as emollients, emulsifiers, surfactants, solubilizers, propellants, solvents, humectants, thickeners and powders. The composition further may comprise a preservative to inhibit microbial outgrowth.

Emollients include alkyl higher fatty acids, natural oils, higher fatty alcohols, glyceryl and isopropyl esters, mineral oils, fatty alcohol esters.

Emulsifiers comprise compounds having a HLB (hydrophilic/lipophilic balance) value which is in the lower or in the higher ranges, i.e. compounds which are able to form a water-in-oil or compounds which are able to form an oil-in-water emulsion, respectively.

Thickeners include polysaccharides, gums and carboxylic group-containing polymers Powders include chalk, talc, starch.

The method of the invention is suitable for any form of topical application, in the cosmetic as well as the dermatological field, wherein the action of an enzyme is required. The method of the invention is particularly suitable for topical application of a protease. Proteases are typically applied in cosmetic compositions for their cleansing, skin smoothening, anti-hairgrowth and anti-acne properties.

EXAMPLE 1

Figure 1:
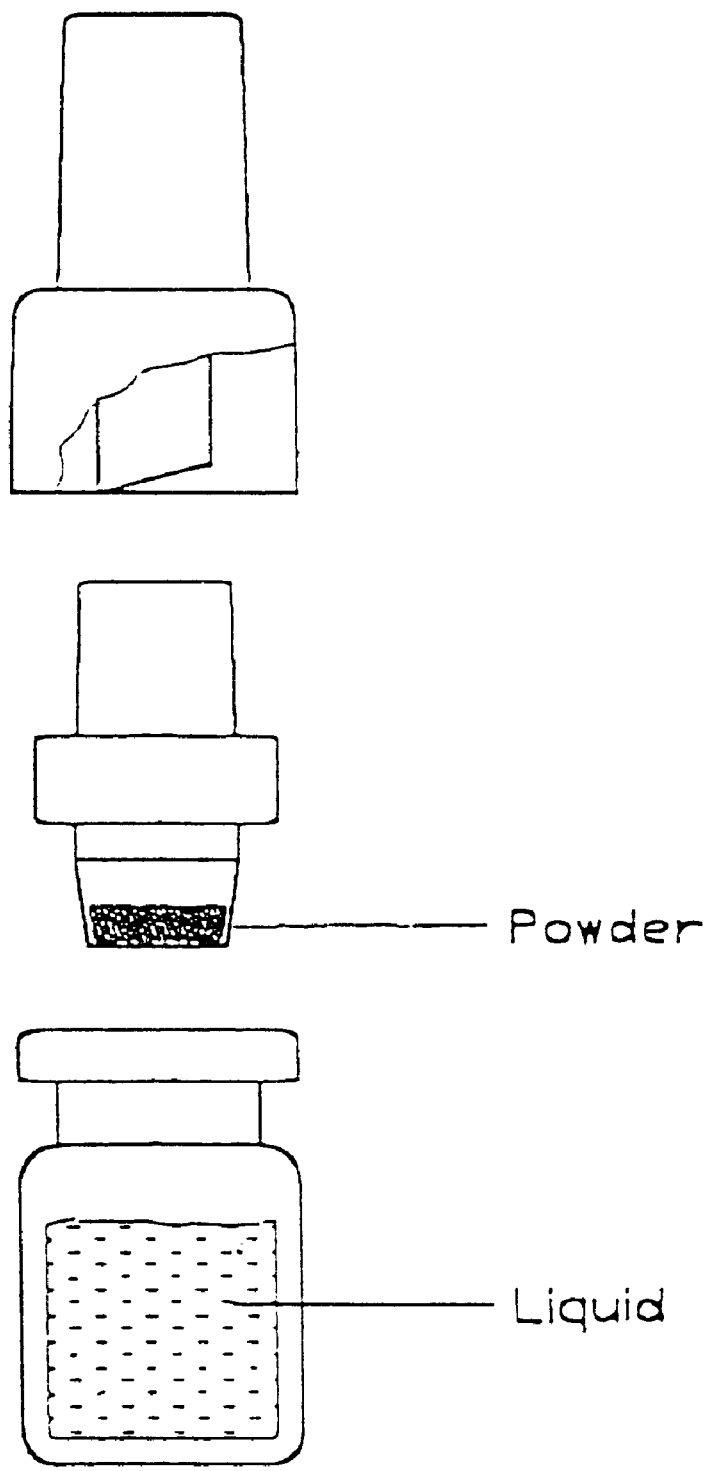
FIGS. 1 and 2. Containers for delivery of two separate compositions.
Figure 2A:
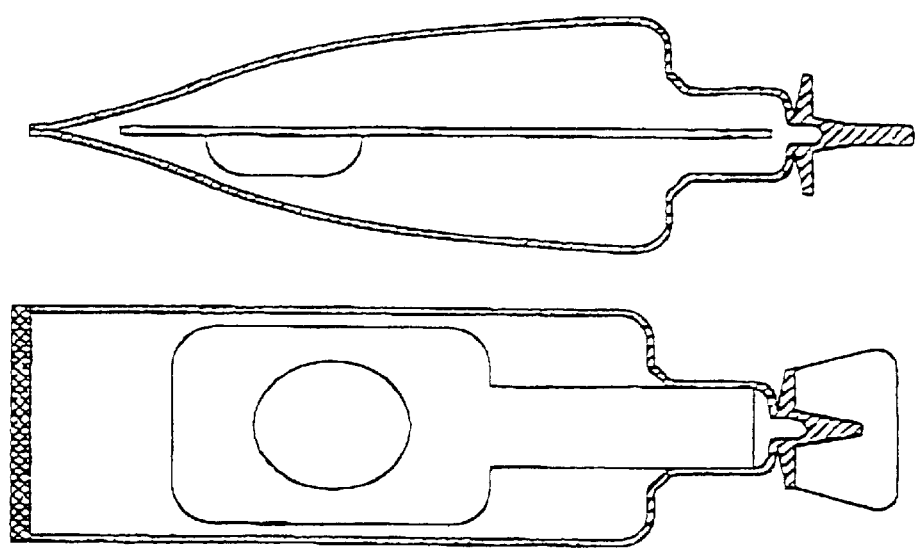
Figure 2B:
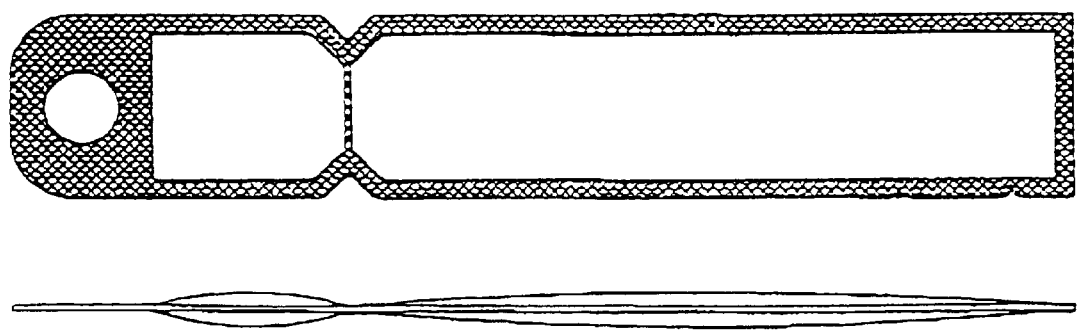

Removal of protease by a PVA film

A protease formulation was prepared by first mixing 35 g of glycerol, 35 g of butylene glycol, 15 mg of calcium chloride.laq, 150 mg sorbic acid, 800 mg of Carbopol Ultrez 10 (BF Goodrich), 160 mg MES (2-N-morpholino-ethane-sulfonic acid) and 16 g of water. Then the pH of the mixture was adjusted to 6.0 using 8N sodium hydroxyde. About 500 mg of protease (Maxatase™, *Bacillus subtilis* alkaline serine protease, 2000 protease Units/mg) was dissolved in the above described mixture and the total weight was adjusted to 100 g by the addition of water.

Maxatase™ powder (2,16 BYU/kg) was obtained from Genencor International (Bruges, Belgium) and was purified to homogeneity using chromatography over a strong cationic gel type resin. The enzyme was applied to the column in 30 mmol/l sodium acetate pH 5.3 and eluted with 100 mmol/l sodium citrate pH 5.8.

Apart from the protease formulation, a PVA formulation was prepared by dissolving 4% Mowiol 40-88 (Clariant) in water.

To test removal of protease enzyme by the PVA film, 1 part of the protease formulation was mixed with 9 parts of the PVA formulation and 4 ml of this protease/PVA mixture was pipetted into a glass beaker. After overnight incubation at 40° C. the water has evaporated and the formed PVA film was removed from the bottom of the glass beaker. After removal of the film, the glass beaker was rinsed with 4 ml of a 50 mM sodium chloride solution.

The protease formulation, the non-soldified protease/PVA mixture and the rinse liquid were analysed for protease activity (by their capacity to hydrolyze casein at pH 7). The results are listed in Table 1.

TABLE 1

Protease activity of the different samples

| Sample | Protease content (Units/g) |
|---|---|
| Protease formulation | 11,200 |
| Protease/PVA mixture | 1,260 |
| Rinse liquid | <4 |

These results clearly indicate that the protease used is active in the PVA solution and that the protease is effectively immobilized into the drying PVA film.

EXAMPLE 2

Protease performance in a protease/PVA mixture

A 50 µl aliquot of the non-solidified protease/PVA mixture as described in Example 1 was brought on the gelatin layer of a photographic film. As a reference sample, a mixture of 1 part of protease formulation (see Example 1) and 9 parts of distilled water was used. The film with the two liquid samples was incubated at 40° C. and protease action was visually inspected after different reaction times. Application of the protease/PVA mixture as well as the reference sample resulted in a completely transparent hole in the gelatine layer after 15 minutes of incubation time. Thus, protease action is not detrimentally influenced by the presence of PVA in the solution.

EXAMPLE 3

Removal of protease from the skin using a PVA film

A protease formulation was prepared by first mixing 35 g of glycerol, 35 g of butylene glycol, 15 mg of calcium chloride.laq, 150 mg sorbic acid, 800 mg of hydroxyethylcellulose, 1 60 mg MES and 1 6 g of water. Then the pH of the mixture was adjusted to 6.0 using 8N sodium hydroxyde. The total weight was adjusted to 1 00 g by the addition of water. Protease powder (*Bacillus subtilis* alkaline serine protease, 4345 protease Units/mg) was dissolved in this mixture in a concentration of 10 mg/ml.

A 4% PVA formulation was prepared by dissolving Mowiol 40-88 in water. The viscosity of this PVA formulation was adjusted by adding 0.8% hydroxyethylcellulose (Natrosol®, Hercules) after which the pH was adjusted to 6.0. 1 part of the protease formulation was mixed with 9 parts of the PVA formulation. About 1 g of this protease/PVA mixture containing 4710 protease Units was applied on the human skin (10 cm² surface area).

After about 45 minutes the water has evaporated and a PVA film could be removed from the skin. After removal of the film, the treated skin was rinsed with 2 ml of a 10 mM MES buffer pH 6.0 also containing 50 mM sodium chloride and 1 mg/ml BSA. The protease/PVA mixture and the rinse liquid were analysed for protease activity and the results are listed in Table 2.

The above described skin application test was carried out on two spots of the volar fore-arm of three test persons.

TABLE 2

Protease removal by PVA

| Sample | Spot | Residual protease (Units) | Protease removed (%) |
|---|---|---|---|
| Test-person 1 | 1 | 38 | 99.2 |
| Test-person 1 | 2 | 36 | 99.2 |
| Test-person 2 | 1 | 24 | 99.5 |
| Test-person 2 | 2 | 30 | 99.4 |
| Test-person 3 | 1 | 32 | 99.3 |
| Test-person 3 | 2 | 26 | 99.4 |

EXAMPLE 4

Performance of films containing high PVA concentrations

The results of this experiment clearly indicate that the peelable film is very efficient in encapsulating free enzyme (in this case protease) and so minimizes the release of enzyme dust particles.

To minimise the water content in PVA films and to increase the tear strength of the film formed, experiments were carried out with low viscosity PVA grades. Starting materials were Mowiol 3-83 and Mowiol 4-88, both from Clariant. After weighing the desired quantity of PVA, the dry material was added to Milli-Q water and heated under constant stirring to 70–80° C. until the PVA was completely dissolved. After addition of sufficient water to reach the desired PVA concentration, the solution was homogenized and cooled down. The pH value of the resulting solution was approx. 6.

The enzyme concentrate was prepared by dissolving purified protease powder in 50 mmol/l MES buffer, pH 6.0; 50 mmol/l NaCl and 2 mmol/l CaCl$_2$. After cooling, each one of the various PVA solutions was mixed with the enzyme concentrate in a ratio of 1 part concentrate per 10 parts PVA solution to reach the PVA concentrations as specified in Table 3. Then the viscosity, spreadability, drying time and proteolytic activity of each solution was determined. Viscosity was determined in a Brookfield DV-III viscosimeter and viscosity was recorded at 25° C. and 50 rpm (Spindle SC 4-29). Proteolytic performance in the PVA mixture was determined by applying aliquots on a photographic film as described in Example 2. The time required to produce a transparent hole in the gelatin layer at 40° C. was used as an indication for proteolytic activity (short incubation period required=high activity; long incubation period required=low activity). The data obtained are shown in Table 3

TABLE 3

| Mowiol type | % (w/w) | viscosity (mPas) | drying time (min) | spreadability | proteolytic activity |
|---|---|---|---|---|---|
| 3-83 | 10 | 10 ± 3 | — | — | 10 min |
| | 20 | 135 ± 3 | 15 | very thin | 10 min |
| | 25 | 308 ± 24 | 16 | reasonable | 10 min |
| | 30 | 966 ± 40 | 20 | good | 20 min |
| | 35 | 3148 ± 51 | 25 | moderate | 20 min |
| | 40 | 7961 ± 33 | 20 | bad | 20 min |
| 4-88 | 10 | 19 ± 3 | — | — | 10 min |
| | 20 | 266 ± 20 | 20 | very thin | 10 min |
| | 25 | 551 ± 18 | 15 | reasonable | 10 min |
| | 35 | 2953 ± 62 | 15 | moderate | 20 min |
| | 35 | 8215 ± 58 | 20 | bad | 20 min |
| | 40 | 25017 | 25 | bad | 20 min |

PVA concentrations between 25 and 35% yield a nicely spreadable mixture. The addition of an additional thickener is not necessary under these conditions. Most important is that under these low water conditions the drying time of the film is very short whereas the proteolytic activity of the mixture is hardly impaired.

EXAMPLE 5

Enzyme removal using an optimised PVA formulation

Apart from increasing the PVA content of the formulation, a quickly evaporating solvent, as for example ethanol, can be incorporated to hasten formation of the PVA film. Additionally, the addition of mild surfactants, as for example Tween 20 (ICI), may further improve the spreadability of the formulation on the skin (e.g. improved wetting) and hence improve removal of the protease from the skin.

One of the selected basic (i.e. without enzyme concentrate added) PVA formulations contained:

Mowiol 3-83 28% (w/w)
Ethanol 10% (w/w)
Tween 201% (w/w)
MilliQ water ad 100

Ethanol was added after complete dissolution and cooling of the Mowiol/Tween formulation. Subsequently, the enzyme concentrate was added in a 1 to 10 ratio as described in Example 4. After careful mixing, the total mixture was applied in a thin layer on the skin (volar forearm) of six test persons. As a reference, a solution containing 0.7% hydroxyethylcellulose and a similar level of of protease was prepared in milliQ water and also applied on the skin of the test persons.

The results obtained with the PVA and the hydroxyethylcellulose solution demonstrated that more than 99% of all protease applied was removed by tearing the dry PVA film from the skin.

This implies a drastic reduction of the risk of allergic sensitisation imposed by enzymatically active cosmetic materials, even if the enzyme used is in a non-immobilised form.

What is claimed is:

1. A method for topical application of an enzyme comprising the steps of preparing a composition comprising a free, non-immobilized enzyme and a film-forming agent;
    applying said composition topically to a skin site;
    incubating said composition on the site of application for a sufficient time period to enable formation of a peelable film incorporating and thereby immobilizing the enzyme; and removing said film incorporating the enzyme from the site of application.

2. The method of claim 1, wherein the composition comprising the enzyme and the film-forming agent is prepared by mixing a separate composition comprising the enzyme and a separate composition comprising the film-forming agent.

3. The method of claim 2, wherein topical application of the composition comprising the enzyme and the film-forming agent is performed by use of a dual component dispensing system.

4. The method of claim 1, wherein the film-forming agent is polyvinyl alcohol (PVA).

5. The method of claim 1, wherein the enzyme is a protease.

6. The method of claim 1 which is a method for cosmetic application.

7. The method according to claim 1, wherein 90% or more of applied enzyme is removed with the peelable film upon removing the peelable film from the skin site.

* * * * *